(12) United States Patent
Bille

(10) Patent No.: US 6,887,232 B2
(45) Date of Patent: *May 3, 2005

(54) CLOSED LOOP CONTROL FOR INTRASTROMAL WAVEFRONT-GUIDED ABLATION

(75) Inventor: Josef Bille, Heidelberg (DE)

(73) Assignee: 20/10 Perfect Vision Optische Geraete GmbH, Heidelberg (DE)

(*) Notice: Subject to any disclaimer, the term of this patent is extended or adjusted under 35 U.S.C. 154(b) by 0 days.

This patent is subject to a terminal disclaimer.

(21) Appl. No.: 10/293,226

(22) Filed: Nov. 13, 2002

(65) Prior Publication Data

US 2004/0092914 A1 May 13, 2004

(51) Int. Cl.$^7$ .............................. A61B 18/18
(52) U.S. Cl. .................. 606/5; 606/4; 606/10; 606/11; 606/12; 351/212
(58) Field of Search ............. 606/4–6, 10–12, 606/17, 18; 351/204–206, 208–216; 128/898

(56) References Cited

U.S. PATENT DOCUMENTS

| | | |
|---|---|---|
| 4,391,275 A | 7/1983 | Fankhauser et al. |
| 4,718,418 A | 1/1988 | L'Esperance, Jr. |
| 4,721,379 A | 1/1988 | L'Esperance |
| 4,770,172 A | 9/1988 | L'Esperance, Jr. |
| 4,907,586 A | 3/1990 | Bille et al. |
| 4,988,348 A | 1/1991 | Bille |
| 6,050,687 A * | 4/2000 | Bille et al. ................. 351/212 |
| 6,095,651 A * | 8/2000 | Williams et al. ........... 351/246 |
| 6,428,533 B1 * | 8/2002 | Bille ........................ 606/11 |

* cited by examiner

Primary Examiner—A. Farah
(74) Attorney, Agent, or Firm—Nydegger & Associates

(57) ABSTRACT

A closed-loop control system for the intrastromal photoablation of tissue includes an active mirror for individually directing the component beams of a diagnostic laser beam to a focal point on the retina of an eye. The reflected beam is analyzed to identify a distorted wavefront indicative of required corneal corrections, and an induced wavefront indicative of optical aberrations introduced by bubbles formed during tissue ablation. A comparator alters the induced wavefront with a desired wavefront to create a rectified wavefront, and a comparator compares the rectified wavefront with the distorted wavefront to create error signals. The error signals are then used to operate the active mirror and to control an ablation laser until the absence of error signals indicate the required stromal tissue has been photoablated.

12 Claims, 2 Drawing Sheets

CLOSED LOOP CONTROL FOR INTRASTROMAL WAVEFRONT-GUIDED ABLATION

FIELD OF THE INVENTION

The present invention pertains generally to laser systems that photoablate corneal tissue to improve the visual acuity of an eye. More particularly, the present invention pertains to laser systems and methods that perform intrastromal photoablation of tissue during corrective optical surgery. The present invention is particularly, but not exclusively, useful as a closed-loop control system to accurately and precisely maintain control of an ablation laser beam when bubbles form in the stroma, and introduce induced optical aberrations during a laser surgery.

BACKGROUND OF THE INVENTION

It is well known that the optical characteristics of an eye can be altered through laser surgery. For example, U.S. Pat. No. 6,050,687 which issued to Bille et al. for an invention entitled "Method and Apparatus for Measuring the Refractive Properties of the Human Eye," and which is assigned to the same assignee as the present invention, discloses a laser system that can be used for such purposes. In any event, a consequence of photoablation, is that individual cells in the tissue are vaporized. Gas is, therefore, a product of photoablation. When a surgical laser procedure involves the superficial photoablation of tissue, the fact that such gases are created does not cause much of a problem. This is not the case, however, when internal tissue is photoablated.

For specific surgical procedures that involve the intrastromal photoablation of corneal tissue, it is known that such photoablation results in the formation of tiny bubbles in the stroma. Further, it is known that the formation of these bubbles introduces induced aberrations that change the optical characteristics of the cornea. The reason for this change is essentially two-fold. First, the gas bubbles have a different refractive index than that of the surrounding stromal tissue. Second, and perhaps more important, the gas bubbles tend to deform the stroma and, thus, they alter its refractive effect on light passing through the cornea. In a controlled surgical procedure these induced aberrations must be accounted for.

Wavefront analysis provides a useful and helpful conceptual tool for determining the effect a particular medium or material (e.g. the cornea of an eye) will have on a light beam, as the beam passes through the medium (material). For wavefront analysis, a light beam can be conveniently considered as being a so-called "bundle" of component light beams. These component light beams are all mutually parallel to each other, and when all of the component beams of a light beam are in phase with each other as they pass through a plane in space, it is said they define a plane wavefront. However, when a light beam passes through a medium, the medium will most likely have a different refractive effect on each of the individual component beams of the light beam. The result is that the phases of the component light beams will differ from each other. When now considered collectively, these component light beams will define something other than a plane wavefront. In summary, a particular wavefront will define the refractive effect a medium, or several media, have had on a light beam.

Insofar as laser surgery is concerned, it is the objective of such surgery to remove unwanted aberrations from the light beams that a patient perceives visually. As implied above, wavefront analysis can be a helpful tool in evaluating and determining the extent to which refractive properties of a cornea may need to be altered or corrected. Indeed, such an analysis has been helpful for surgical procedures involving superficial photoablation. For example, U.S. Pat. No. 6,428,533B1 which issued to Bille for an invention entitled "Closed Loop Control for Refractive Laser Surgery (LASIK)," and which is assigned to the same assignee as the present invention, discloses such a system.

As recognized by the present invention, when intrastromal photoablation is to be performed, and the evaluations and determinations of a wavefront analysis are put into practice, it is desirable to establish control over each individual component beam defining a wavefront. With this control, induced aberrations such as mentioned above, can be accurately compensated for, and the overall control of the procedure is enhanced.

SUMMARY OF THE INVENTION

In accordance with the present invention, a closed-loop system is provided which will control the photoablation of stromal tissue in an eye during an intrastromal surgical procedure. More specifically, in addition to controlling the photoablation of the stromal tissue that is necessary for a corrective procedure, the control system of the present invention also compensates for optical aberrations that are induced by gas bubbles as they form in the stromal tissue that is being photoablated.

For purposes of wavefront analysis, a light beam is properly considered as including a plurality of individual component beams. Collectively, these constituent component light beams define a wavefront for the larger inclusive light beam. With this in mind, and in the context of the present invention, several definitions for light beam wavefronts are helpful. Specifically, these definitions pertain after a light beam has passed through the stroma of an eye. A "desired wavefront" results from the stroma of a corrected eye, and is the objective of a surgical procedure. A "distorted wavefront" results from the stroma of an uncorrected eye, and exhibits the actual real-time characteristics of the cornea, before correction. An "induced wavefront" results from the formation of bubbles in the stroma, and includes the "distorted wavefront." A "rectified wavefront" results by incorporating an "induced wavefront" with a "desired wavefront."

Structurally, the system of the present invention includes two distinct laser sources. One is for generating an ablation laser beam that will be used to photoablate stromal tissue. The other is for generating a diagnostic laser beam. Conceptually, as mentioned above, the diagnostic laser beam is properly considered as including a plurality of individual component beams.

Along with the two laser sources just mentioned, the system of the present invention also includes an active mirror and a detector. More specifically, the active mirror comprises a plurality of separate reflective elements for individually reflecting respective component beams of the diagnostic beam. Together, these elements of the active mirror are used, in concert, to direct the diagnostic laser beam to a focal spot on the retina of the eye. The detector is then used to receive the diagnostic beam after it has been reflected from the retina.

In the operation of the present invention, a compensator incorporates a desired wavefront (predetermined for the patient), with the induced wavefront as it is received by the detector. This incorporation creates a rectified wavefront. A comparator is then used to compare the rectified wavefront with the distorted wavefront (diagnostically predetermined) to create an error signal. Consistent with the wavefront analysis used to define light beams, the error signal is properly considered as having a plurality of error segments. These error segments are then used by the system of the present invention to individually activate a respective reflective element of the active mirror, and to thereby maintain the focal spot of the diagnostic beam on the retina. The ablative laser source can then be continuously operated to photoablate stromal tissue using a so-called "spot-by-spot" local ablation strategy until the error signal is substantially a nullity.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
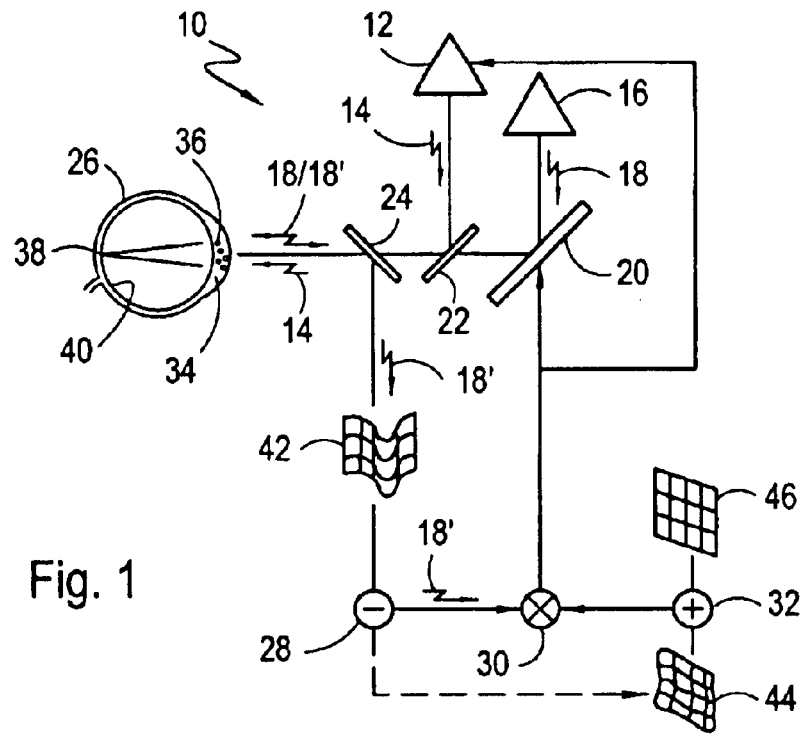
FIG. 1 is a schematic layout showing the interrelationships of components in a system for controlling the intrastromal photoablation of corneal tissue in an eye in accordance with the present invention.

Referring initially to FIG. 1, a closed-loop system for intrastromal photoablation of corneal tissue in accordance with the present invention is shown and is generally designated 10. In detail, the components of system 10 include a source 12 for generating an ablation laser beam 14, and a source 16 for generating a diagnostic laser beam 18. Further, the system 10 includes an active, multi-facet mirror 20, a beam splitter 22 and a beam splitter 24. More particularly, the active mirror 20 is preferably of a type disclosed in U.S. Pat. No. 6,220,707 which issued to Bille for an invention entitled "Method for Programming an Active Mirror to Mimic a Wavefront" and which is assigned to the same assignee as the present invention. As shown, the active mirror 20 and the beam splitters 22 and 24 direct the diagnostic laser beam 18 from diagnostic laser source 16 toward an eye 26. Likewise, the beam splitters 22 and 24 are used to direct the ablation laser beam 14 from the ablation laser source 12 toward the eye 26.

FIG. 1 also shows that the system 10 of the present invention includes a detector 28, a comparator 30 and a compensator 32. In particular, the detector 28 is preferably of a type commonly known as a Hartmann-Shack sensor. The comparator 30 and compensator 32 are electronic components known in the pertinent art that will perform the requisite functions for the system 10.

Still referring to FIG. 1, it is to be appreciated and understood that during an intrastromal photoablation procedure, as performed by the system 10 of the present invention, the ablation laser beam 14 is focused (by optical components not shown) onto stromal tissue 34 in the cornea of the eye 26 for the purpose of accomplishing intrastromal photoablation. A consequence of this photoablation of the tissue 34 is the formation of gas bubbles 36 that introduce optical aberrations in the stromal tissue 34. At the same time, the diagnostic laser beam 18 is focused (by optical components not shown) to a focal spot 38 on the retina 40 of the eye 26. In this combination, control by the system 10 over the ablation laser beam 14 is actually accomplished using the reflected diagnostic laser beam 18', as it is reflected through the stromal tissue 34 from the focal spot 38 on the retina 40 of eye 26.

FIG. 1 shows that as the reflected diagnostic laser beam 18' exits from the eye 26 through the stromal tissue 34, the beam 18' is directed by beam splitter 24 toward the detector 28. Using wavefront analysis considerations, the reflected diagnostic beam 18' can be conceptually considered as including a plurality of individual and separate laser beam components. Together, these components can be characterized as a distorted wavefront 42. Further, this distorted wavefront 42 will result from two contributions. One contribution results from the uncorrected eye 26 and is an actual real-time consequence of light passing through the stromal tissue 34. It is this contribution that is to be corrected. The other contribution results from the aberrations that are introduced by the presence of the gas bubbles 36 in the stromal tissue 34. Again using wavefront analysis, the contribution introduced by the gas bubbles 36 can be conceptualized as a wavefront having a plurality of components that are collectively characterized as an induced wavefront 44, FIG. 1 further shows a desired wavefront 46. This desired wavefront 46 will most likely be either a plane wavefront, or a wavefront that is relatively similar to a plane wavefront. In any event, it is the desired wavefront 46 that is the objective of the procedure to be performed by the system 10.

Figure 2:
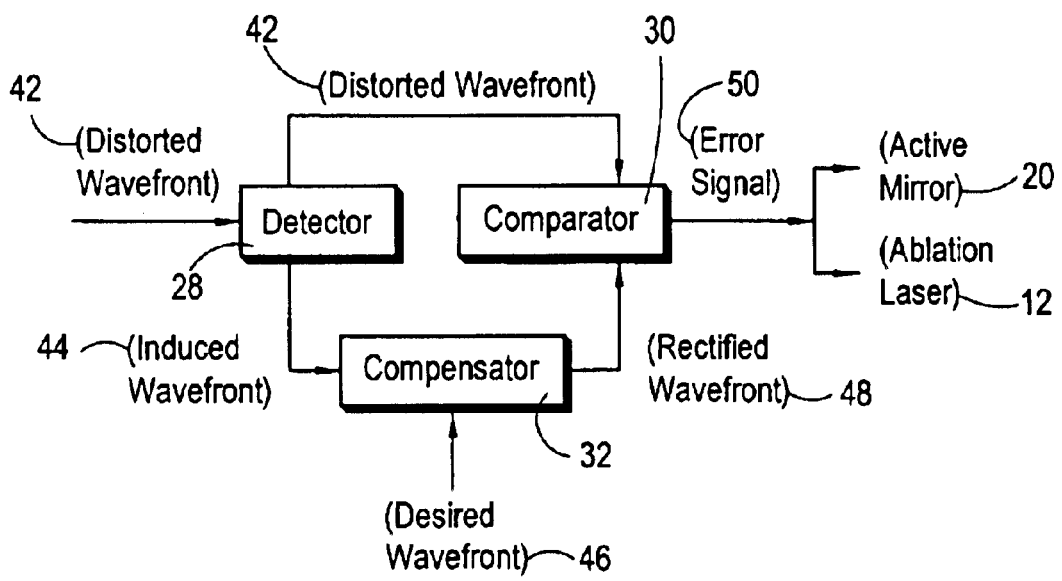
FIG. 2 is a functional representation of the wavefront analysis techniques used in the operation of the system of the present invention.

By cross referencing FIG. 1 with FIG. 2, it will be appreciated that in the operation of the system 10, the distorted wavefront 42 is first received by the detector 28. Using predetermined diagnostic information about the corrections that are to be made to the eye 26 by system 10, the detector 28 determines and generates the induced wavefront 44. The compensator 32 then alters a predetermined, desired wavefront 46 with this induced wavefront 44. This alteration creates a rectified wavefront 48. The rectified wavefront 48 is then compared with the distorted wavefront 42 to generate an error signal 50. In turn, this error signal 50 is used to manipulate the active mirror 20 for control of the diagnostic laser beam 18. Importantly, the error signal 50 is also used to activate the ablation laser source 12 and, specifically, the error signal 50 causes the ablation laser source 12 to cease its operation when the error signal 50 is a null.

Figure 3:
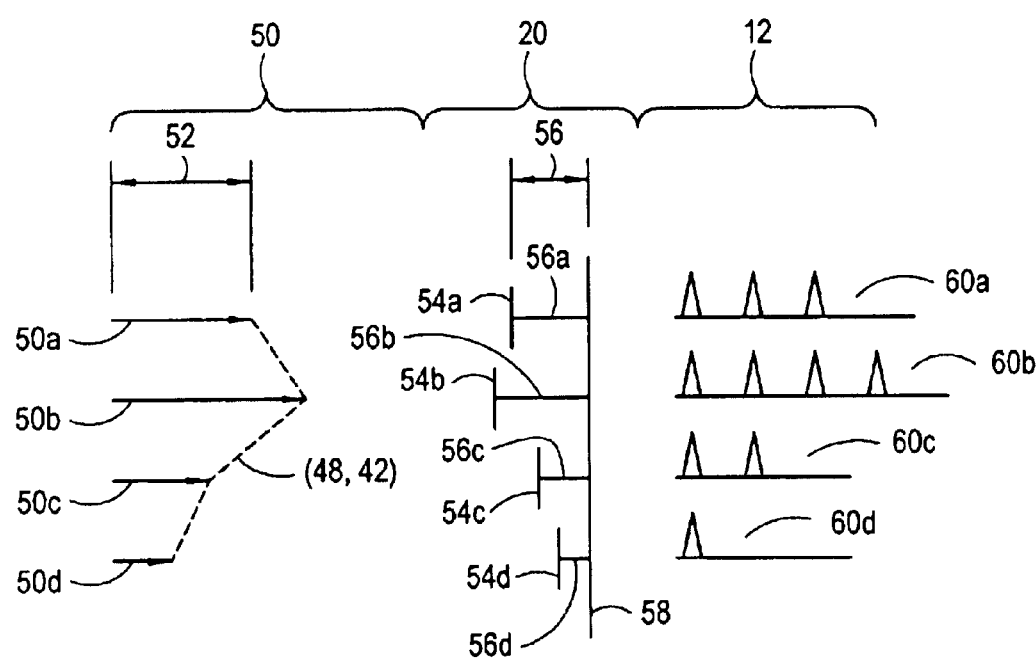
FIG. 3 is a schematic representation of the interrelationships between the component beams of a wavefront, corresponding reflective elements of the active mirror, and required laser pulses from the ablation laser source.

In response to the error signal 50, the operation of the active mirror 20, as well as the operation of ablation laser source 12 will, perhaps, be best appreciated with reference to FIG. 3. Again, using a wavefront analysis, the error signal 50 can conceptually be considered as comprising a plurality of component error signals. For this analysis, the component error signals 50a, 50b, 50c and 50d shown in FIG. 3 are only exemplary. In general, what is important here, is that each of the exemplary component error signals 50a–d result from the interaction of corresponding components of the wavefronts 42, 44, 46 and 48. As disclosed above, these wavefronts 42, 44, 46 and 48 directly result from the refraction of corresponding beam components of the diagnostic laser beam 18. Stated differently, each component beam of the diagnostic laser beam 18 is present in each of the wavefronts: namely, the distorted wavefront 42, the induced wavefront 44, the desired wavefront 46, and the rectified wavefront 48. Consequently, each component beam of the diagnostic laser beam 18 generates a corresponding error signal component 50a–d. Depending on its refractive history as it passes through the system 10, each error signal component 50a–d will have a respective magnitude 52.

FIG. 3 also indicates that the active mirror 20 includes a plurality of reflective elements 54, of which the reflective elements 54a–d are exemplary. FIG. 3 also indicates that each reflective element 54 is at a respective distance 56 (i.e. distances 56a–d) from a datum 58. For example, each; error signal component 50 (e.g. error signal component 50a) is used by the system 10 to establish a respective distance 56 for a corresponding reflective element 54 of the active mirror 20 (e.g. signal 50a and distance 56a).

FIG. 3 also shows that the ablation laser source 12 will generate a plurality of separate laser pulse trains 60 that correspond to each corresponding error signal component 50a–d. For instance, the error signal component 50a, will generate a laser pulse train 60a. The laser pulse train 60a is then continued until the error signal component 50a is a null. Similarly, the pulse trains 60b–d react to corresponding error signal components 50b–d. While this is happening to ablate the stromal tissue 34, the; error signal components 50a–d also interact with the active mirror 20. Specifically, as the error signal component 50a decreases in its magnitude 52, the distance 56 of reflective element 54a from datum 58 also decreases. This, is done to maintain the focal spot 38 fixed on the retina 40 of eye 26 so that the distorted wavefront 42 is maintained as an accurate measure of the progress of the intrastromal photoablation procedure. The ablation laser source 12 is inactivated, when all of the error signal components 50a–d (i.e. error signal 50) are a nullity.

While the particular Closed Loop Control for Intrastromal Wavefront-Guided Ablation as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A closed-loop system for controlling intrastromal photoablation of stromal tissue of an eye, wherein gas bubbles resulting from the ablation of the tissue introduce induced optical aberrations, said system comprising:

a source for generating an ablation laser beam to photoablate stromal tissue;

a source for generating a diagnostic laser beam, with the diagnostic laser beam including a plurality of component beams;

an active mirror for directing said diagnostic laser beam to a focal spot on the retina of the eye;

a detector for using light of said diagnostic beam reflected from the retina through the bubbles to generate an induced wavefront having characteristics of the induced optical aberrations, together with a distorted wavefront having actual real-time characteristics of the cornea;

a compensator for altering a predetermined desired wavefront by incorporating said induced wavefront therewith to create a rectified wavefront;

a comparator for comparing said rectified wavefront with said distorted wavefront to create an error signal having a plurality of error segments;

a means for reconfiguring said active mirror in response to said plurality of error segments to maintain said focal spot on the retina, wherein said active mirror comprises a plurality of separate reflective elements for individually reflecting respective component beams of the diagnostic beam, and wherein said reconfiguring means individually activates each said reflective element in response to a corresponding segment of said error signal; and a means for ceasing generation of said ablation beam when said error signal is substantially a nullity.

2. A system as recited in claim 1 wherein said ablation beam is a pulsed laser beam.

3. A system as recited in claim 1 wherein said detector is a Hartmann-Shack sensor unit.

4. A system as recited in claim 1 wherein said desired wavefront is a plane wavefront.

5. A closed-loop system for controlling intrastromal photoablation of tissue in the cornea of an eye, wherein gas bubbles resulting from the ablation of the tissue introduce induced optical aberrations, said system comprising:

a means for detecting an induced wavefront indicative of light passing through the cornea, said induced wavefront including characteristics of the induced optical aberrations;

a means for altering said induced wavefront with a desired wavefront to obtain a rectified wavefront having a plurality of components;

a means for comparing said components of the rectified wavefront with a predetermined distorted wevefront to create an error signal having a plurality of error segments respectively corresponding to components of the rectified wavefront;

a means for using said error signal to activate an ablation laser beam for ablating stromal tissue; and a means for ceasing generation of the ablation laser beam when au error segments of the error signal are a null.

6. A system as recited in claim 5 wherein said detecting means comprises:

a source for generating a diagnostic laser beam, with the diagnostic laser beam including a plurality of component beams;

an active mirror for directing said diagnostic laser beam to a focal spot on the retina of the eye; and a detector for using light of said diagnostic beam reflected from the retina through the bubbles to generate respective components for an induced wavefront having characteristics of the induced optical aberrations.

7. A system as recited in claim 6 wherein the detector is a Hartmann-Shack sensor.

8. A system as recited in claim 6 wherein the active mirror comprises a plurality of separate reflective elements for individually reflecting respective component beams of the diagnostic beam.

9. A system as recited in claim 8 wherein the active mirror maintains the focal spot on the retina by separately reconfiguring the reflective elements in response to respective error segments in the error signal.

10. A method for controlling the intrastromal photoablation of tissue of an eye, wherein gas bubbles resulting from, the ablation of tissue introduce induced optical aberrations, the method comprising the steps of:

predetermining a desired wavefront for the eye;

generating a diagnostic laser beam, with the diagnostic laser beam including a plurality of component beams;

using an active mirror to direct the diagnostic laser beam to a focal spot on the retina of the eye, the active mirror having a plurality of separate reflective elements for individually reflecting respective component beams of the diagnostic beam;

using the components of the diagnostic laser beam to identify respective components of an induced wavefront, the induced wavefront being characteristic of the induced optical aberrations;

altering the desired wavefront with the components of the induced wavefront to create a rectified wavefront having respective components;

detecting components of a distorted wavefront with light from the diagnostic beam reflected from the retina, the distorted wavefront having actual real-time characteristics of the cornea;

comparing components of the rectified wavefront with respective components of the distorted wavefront to create a plurality of error segment signals;

reconfiguring respective reflective elements of the active mirror in accordance with the error segment signals to maintain the focal spot of the diagnostic laser beam on the retina;

selectively generating an ablation beam to photoablate stromal tissue; and ceasing generation of the ablation laser beam when the error segment signals are a null.

11. A method as recited in claim 10 wherein the ablation laser beam is a pulsed laser beam.

12. A method as recited in claim 10 wherein the desired wavefront is a plane wavefront.

* * * * *

UNITED STATES PATENT AND TRADEMARK OFFICE
CERTIFICATE OF CORRECTION

PATENT NO. : 6,887,232 B2
DATED : May 3, 2005
INVENTOR(S) : Joseph Bille

It is certified that error appears in the above-identified patent and that said Letters Patent is hereby corrected as shown below:

Column 1,
Line 47, delete "too)" insert -- tool --
Line 56, delete "fight" insert -- light --

Column 4,
Line 30, delete "44," insert -- 44 --

Column 5,
Line 11, delete "each;" insert -- each --

Signed and Sealed this

Nineteenth Day of July, 2005

JON W. DUDAS
*Director of the United States Patent and Trademark Office*